(12) United States Patent
Ozaki et al.

(10) Patent No.: US 6,319,473 B1
(45) Date of Patent: Nov. 20, 2001

(54) CO SENSOR AND ITS FABRICATION

(75) Inventors: Yasutaka Ozaki; Sachiyo Suzuki, both of Osaka (JP)

(73) Assignee: Figaro Engineering, Inc., Osaka (JP)

( * ) Notice: Subject to any disclaimer, the term of this patent is extended or adjusted under 35 U.S.C. 154(b) by 0 days.

(21) Appl. No.: 09/332,877

(22) Filed: Jun. 15, 1999

(30) Foreign Application Priority Data

Jun. 16, 1998 (JP) .................................................. 10-186967

(51) Int. Cl.⁷ .......................... G01N 27/26; G01N 33/00; G01N 29/00; G01N 27/12
(52) U.S. Cl. ................... 422/88; 422/98; 422/83; 422/80; 422/89
(58) Field of Search ........................ 422/88, 98; 736/121; 204/424, 1; 156/89; 73/23.31; 340/632; 431/7

(56) References Cited

U.S. PATENT DOCUMENTS

| | | | |
|---|---|---|---|
| 3,966,391 | * | 6/1976 | Hindin et al. ............................ 431/7 |
| 4,267,023 | * | 5/1981 | Frant et al. ............................... 204/1 |
| 5,528,225 | * | 6/1996 | Sakai et al. .......................... 340/632 |
| 5,589,046 | * | 12/1996 | Li et al. ................................. 204/424 |
| 5,759,367 | * | 6/1998 | Matsuura et al. ..................... 204/424 |
| 5,762,737 | * | 6/1998 | Blonik et al. ............................ 156/89 |
| 5,948,965 | * | 9/1999 | Upchurch et al. .................... 73/23.31 |
| 5,980,833 | * | 11/1999 | Higaki et al. ........................... 422/98 |
| 6,046,054 | * | 4/2000 | McGeehin et al. ................... 436/121 |

FOREIGN PATENT DOCUMENTS

| | | |
|---|---|---|
| 1-207653 | 8/1989 | (JP) . |
| 4-279853 | 10/1992 | (JP) . |

* cited by examiner

*Primary Examiner*—Jill Warden
*Assistant Examiner*—Brian J. Sines
(74) *Attorney, Agent, or Firm*—Arent Fox Kintner Plotkin & Kahn, PLLC (57) ABSTRACT

After sintering of a CO sensor using an SnO2-based metal oxide semiconductor, Ir and Pt are added to the sensor at 5~500 µg/g SnO2 each, the weight ratio of Ir and Pt being 5~1/5. This addition is made by impregnating a mixed aqueous solution of an Ir salt and a Pt salt into the SnO2 sintered body and thermally decomposing these salts. Next, an aqueous solution of thiourea is impregnated into the SnO2 sintered body to add thiourea at 0.01~10 mg/g SnO2 in reduction to simple S element. The temperature and humidity dependency of the CO sensor is suppressed, the CO concentration dependency of the output is increased, and the sensor resistance is brought to a more convenient range of use.

10 Claims, 13 Drawing Sheets

Prior Art

FIG. 5

Prior Art

Prior Art

Prior Art

FIG. 1 1

Prior Art

Prior Art

FIG. 14

Prior Art

Prior Art

FIG. 19

CO SENSOR AND ITS FABRICATION

FIELD OF THE INVENTION

The present invention relates to a CO sensor using an SnO2 metal oxide semiconductor and a method of production thereof.

PRIOR ART

It is known that an SnO2-based CO sensor is subjected to a higher temperature and a lower temperature alternately and the level of CO is detected from an output of the CO sensor at the lower temperature. For example, in the case of the present applicant's SnO2-based gas sensor TGS203 (TGS203 is a trade name), a pair of electrodes also serving as heaters are buried in a sintered body of SnO2 and the gas sensor is operated at a cycle of 150 seconds. The gas sensor is heated to a higher temperature (the highest temperature is 300° C. approx.) in the first 60 seconds and to a lower temperature (the lowest temperature is 80° C. approx.) in the subsequent 90 seconds. CO level is detected from a sensor signal that is generated immediately before the end of the lower temperature period. In this gas sensor, 2 mg approx. of Pd in reduction to metal is added to 1 g of SnO2.

SnO2-based CO sensors, however, tend to increase in resistance about two times within the first several months after the start of service.

SUMMARY OF THE INVENTION

A primary task of the present invention is to prevent long-term increase in CO sensor resistance.

A secondary task of the present invention is to improve CO concentration dependency of the resistance of the CO sensor.

Another task of the present invention is to suppress temperature and humidity dependency of the CO sensor.

The CO sensor according to the present invention is a sensor that detects CO including SnO2 gas sensitive material subjected to cyclical temperature change, wherein 0.01~10 mg/gSnO2 of an electron-donative sulfur compound in reduction to simple S element is added in said SnO2.

Preferably, the addition of said sulfur compound is 0.1~5 mg/gSnO2 in reduction to simple S element.

Preferably, said electron-donative sulfur compound is at least one member of a group consisting of thiourea, thiosulfuric acid and its derivatives, thiocyanic acid and its derivatives, thiocyanogen and its derivatives, thiol, thiophenol, thioether, thiosugar and its derivatives, thiophene and its derivatives, thionaphthene and its derivatives, thiotolene and its derivatives, thiopyran and its derivatives, thiophthene and its derivatives, thioacetazone and its derivatives, thioxene and its derivatives, thioacetal and its derivatives, thioindigo and its derivatives, thiooxine and its derivatives, thiocarbazide and its derivatives, thiokinase, thioglucosidase and CS2. Most preferably, said electron-donative sulfur compound is at least a member of a group of compounds comprising thiourea, thiosulfuric acid and its derivatives, for example, ammonium thiosulfate, thiocyanic acid and its derivatives, for example, ammonium thiocyanate, thiocyanogen and its derivatives.

Preferably, in said SnO2, 5~500 µg/gSnO2 of Ir in reduction to metal is added.

Further, preferably, said Ir is added in the form of an Ir-Pt compound catalyst wherein the additions of Ir and Pt are respectively 5~500 µg/gSnO2 each in reduction to metal, and the weight ratio of Ir to Pt is from 1/5 to 5.

In the method of production of the CO sensor of the present invention, after SnO2 powder being a gas sensitive material is sintered, 0.01~10 mg/gSnO2 of an electron-donating sulfur compound in reduction to simple S element is added. Said electron-donative sulfur compound includes, for example, thiourea, thiosulfuric acid and its derivatives, thiocyanic acid and its derivatives, thiocyanogen and its derivatives, thiol, thiophenol, thioether, thiosugar and its derivatives, thiophene and its derivatives, thionaphthene and its derivatives, thiotolene and its derivatives, thiopyran and its derivatives, thiophthene and its derivatives, thioacetazone and its derivatives, thioxene and its derivatives, thioacetal and its derivatives, thioindigo and its derivatives, thiooxine and its derivatives, thiocarbazide and its derivatives, thiokinase, thioglucosidase and CS2. Preferably, said electron-donative sulfur compounds is at least a member of a group comprising thiourea, thiosulfuric acid and its derivatives, for example, ammonium thiosulfate, thiocyanic acid and its derivatives, for example, ammonium thiocyanate, thiocyanogen and its derivatives.

Preferably, a solution of said electron-donative sulfur compound is impregnated into a sintered body of SnO2, and after that, the sintered body is dried and heat-treated. Most preferably, both Ir and Pt, 5~500 µg/gSnO2 in reduction to metal each, are added, the weight ratio of Ir/Pt being from 1/5 to 5, by impregnating a mixed solution of an Ir compound and a Pt compound into a sintered body of SnO2, then decomposing the Ir compound and the Pt compound impregnated.

With regard to the kind of CO sensor, for example, both the higher temperature and the lower temperature of a CO sensor may be higher than room temperature, and electric power may be given to the heater of the CO sensor in both the lower temperature period and the higher temperature period. The higher temperature of a CO sensor may be, for example, 300° C. approx., and a heating time to achieve the higher temperature may be, for example, from 10 ms to 10 s, and a standing time to the lower temperature may be, for example, from 1 s to 100 s, and the heater power may be set at 0 in the lower temperature period, allowing naturally cooling of the CO sensor down to around room temperature. In other words, with regard to the kind itself of CO sensor, it is sufficient that the sensor is an SnO2-based CO sensor that uses cyclic temperature change.

According to the present invention, 0.01~10 mg/gSnO2 of an electron-donative sulfur compound, in reduction to simple S element, is added being a gas sensitive material. This suppresses the long-term resistance increase of the CO sensor. Addition of 0.1 mg/gSnO2 or more of an electron-donative sulfur compound can eliminate the long-term resistance increase almost entirely. As a result, a CO sensor of extremely high reliability can be obtained. The addition of an electron-donative sulfur compound at said rate increases the CO concentration dependency α of the resistance of the CO sensor, and in turn, improves its quantitativeness. When the sensor resistance is denoted by Rs, the CO concentration dependency α is defined by $$Rs = k \cdot [CO]^{-\alpha} \text{(where } k \text{ is a constant of proportion)} \qquad (1)$$

The sulfur compound to be added is at least one member of a group comprising, for example, thiourea, thiosulfuric acid and its derivatives, for example, ammonium thiosulfate, thiocyanic acid and its derivatives, for example, ammonium thiocyanate and isothiocyanic acid, methyl thiocyanate and ethyl thiocyanate, allyl isothiocyanate, thiocyanogen and its derivatives, for example, various rhodan compounds and dichloroiminodithiazolidine, thiol, thiophenol, thioether, thiosugar such as D glucothiose, methyl thioadenosine and its derivatives, thiophene and its derivatives, thionaphthene and its derivatives, thiotolene and its derivatives, thiopyran and its derivatives, thiophthene and its derivatives, thioacetazone and its derivatives, thioxene and its derivatives, thioacetal and its derivatives, thioindigo and its derivatives, thiooxine and its derivatives, thiocarbazide and its derivatives, thiokinase, thioglucosidase and CS2. Preferably, the sulfur compound to be added is at least one member of a group consisting of thiourea, thiosulfuric acid and its derivatives, for example, ammonium thiosulfate, thiocyanic acid and its derivatives, for example, ammonium thiocyanate, and thiocyanogen and its derivatives. These sulfur compounds are electron-donative. For example, in the case of thiosulfuric acid, an S atom at a vertex of a tetrahedron around the central sulfur atom is electron-donative. These sulfur compounds have a sulfur atom of which oxidation number is 2 or under, in particular, −2. Of these compounds, thiourea, thiosulfuric acid and its derivatives, thiocyanic acid and its derivatives, and thiocyanogen and its derivatives have sulfur of which oxidation number is −2 and their sulfur atoms are double-bonded.

Addition of these sulfur compounds differ from addition of sulfate ion, etc. In the case of addition of sulfate ion, the effect of suppressing the long-term resistance increase of a CO sensor is small. In contrast, addition of an electron-donative sulfur compound can prevent the long-term resistance increase almost completely. Further, addition of an electron-donative sulfur compound can improve the CO concentration dependency α, while additon of sulfate ion results in a decrease of in many cases. Addition of a sulfur compound is made, for example, after sintering of an SnO2-based gas sensitive body.

Ir is added together with an electron-donative sulfur compound. Ir increases α of the CO sensor greatly, increases its resistance, and increases the tendency of the long term resistance increase. The electron-donative sulfur compound suppresses the long-term resistance increase and also suppresses increase in the resistance. Addition of Ir—Pt results in an increase in α and a decrease in the temperature and humidity dependency. Addition of Ir—Pt and an electron-donative sulfur compound has effects of suppressing the temperature and humidity dependency, increasing α, preventing the long-term resistance increase, and achieving a convenient range of resistance.

The form of existence of the electron-donative sulfur compound in SnO2 is not known. It is not certain whether the increase in α and the suppression of the long-term resistance increase are caused by continued presence of the electron-donative sulfur compound in SnO2 or effects of the sulfur compound on the particle form of SnO2 particles at the time of addition, in particular, effects on the ceramic structure of the gas sensitive body after sintering. The electron-donative sulfur compound and Ir or Ir—Pt may be added simultaneously or separately.

Furthermore, phosphate ion may be added to SnO2 to improve the relative sensitivity to CO in comparison to its sensitivity to hydrogen.

EMBODIMENT

Figure 1:
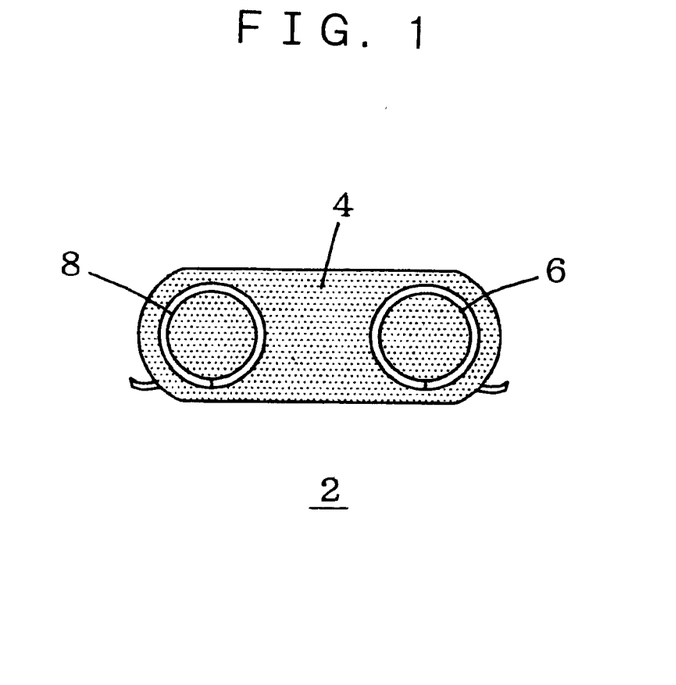
FIG. 1 is a sectional view of a gas sensor of an embodiment.
Figure 2:
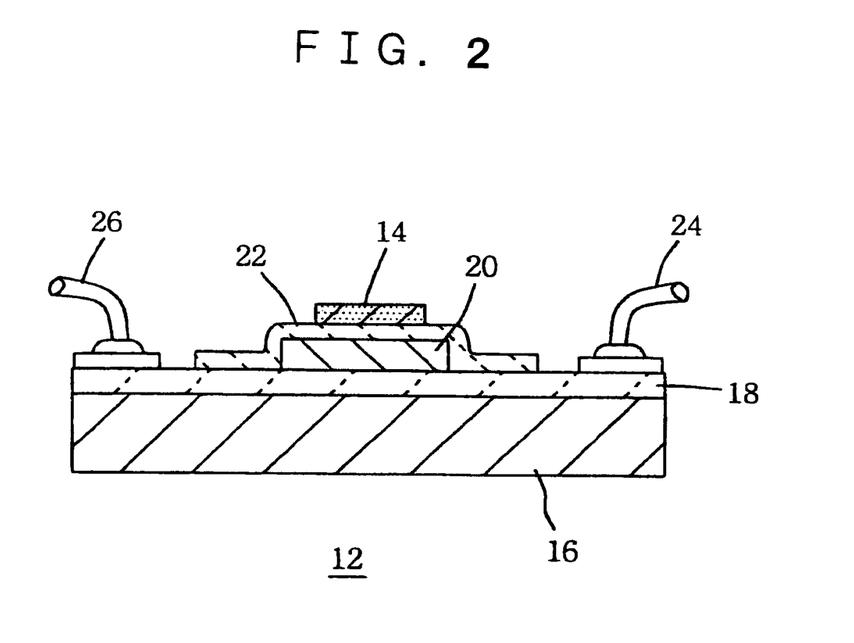
FIG. 2 is a sectional view of a gas sensor of a modification.

FIG. 1 shows the structure of a gas sensor of an embodiment, and FIG. 2 shows the structure of a gas sensor of a modification. FIG. 3 through FIG. 18 show characteristics of the gas sensor of the embodiment and the gas sensor of the modification. In FIG. 1, 2 denotes a gas sensor, 4 denotes a metal oxide semiconductor wherein SnO2 being a gas sensitive material is sintered, and 6 and 8 are a pair of coil electrodes also serving as heaters. The metal oxide semiconductor 4 is, for example, a mixture of SnO2 and alumina at a weight ratio of 1/1 approx. After sintering of the metal oxide semiconductor 4, an aqueous solution of thiourea or an aqueous solution of ammonium thiosulfate, etc., being an electron-donative S compound, is dropped to the metal oxide semiconductor 4. After drying, the semiconductor 4 is heated, for example, in atmosphere at 600° C. for 10 minutes. Then an aqueous solution of Ir nitrate or a mixed aqueous solution of Ir nitrate and chloroplatinic acid is impregnated into the semiconductor 4. Next, the semiconductor S is heated, for example, in atmosphere at 600° C. to make thermal decomposition and add Ir or Ir—Pt.

The gas sensor of FIG. 1 is operated at a cycle of 150 seconds. The period of a higher temperature is 60 seconds and the highest temperature (at the end of the higher temperature period) is 300° C. The period of a lower temperature is 90 seconds and the lowest temperature (at the end of the lower temperature period) is 80° C. CO level is detected from a sensor signal (sensor resistance Rs) that is generated immediately before the end of the lower temperature period.

The structure itself of the gas sensor is arbitrary provided SnO2 is the gas sensitive material and the sensor is subjected to cyclical temperature change. For example, in a gas sensor 12 of the modification shown in FIG. 2, a glass film 18 for heat insulation is laminated on a base material 16 of alumina, etc., and a thick film heater 20 of RuO2, etc. is provided. Then the heater 20 is covered by an insulating film 22 of glass film, etc. On this insulating film 22, an SnO2-based metal oxide semiconductor 14 is built into a thick film of, for example, 20 $\mu$m thick. Leads 24, 26, etc. are connected to the heater 20 and the metal oxide semiconductor 14 via electrode pads. The gas sensor of FIG. 2 is heated up to 300° C. approx. by, for example, applying power to the heater 20 for 10 ms~1 s. After that, the gas sensor is allowed to cool down to around room temperature by, for example, turning off the heater 20 for 1~100 s. During this period, CO level is detected from the sensor resistance, for example, one second after or 10 seconds after turning off the heater 20.

In the gas sensor 12 of FIG. 2, the SnO2-based metal oxide semiconductor 14 is sintered, for example, at 600° C., and after that, a solution of an electron-donative S compound is added, then after drying, the semiconductor 14 is heated, for example, in atmosphere at 600° C. Next, a solution of an Ir compound or a mixed solution of an Ir compound and a Pt compound, etc. is impregnated into the semiconductor 14, and the solution is subjected to thermal decomposition in atmosphere at 600° C. to add Ir or Ir—Pt. The effects of an electron-donative S compound and the effects of Ir or Ir—Pt in the gas sensor 2 of FIG. 1 are comparable to the effects of an electron-donative S compound and the effects of Ir or Ir—Pt in the gas sensor 12 of FIG. 2. In the following, an example of production of the gas sensor of FIG. 1 and its characteristics are described.

An aqueous solution of SnCl4 was neutralized with ammonia. The precipitation was dried, then it was subjected to thermal decomposition in atmosphere at 700° C. for one hour to produce SnO2. An aqua regia solution of Pd was added to this SnO2 so that the addition of Pd in reduction to metal was 2 mg/gSnO2. After drying, SnO2 was calcined to carry Pd. In place of Pd, an appropriate noble metal catalyst, such as Pt, Rh and Au, may be added. Further, V or sulfate ion may be added. After SnO2 was made to carry a catalyst, SnO2 was crushed and mixed with alumina powder being equal in weight, then the mixture was molded into the configuration of the gas sensor of FIG. 1 and sintered in atmosphere, for example, at 700° C. for 10 minutes. Next, an aqueous solution of thiourea or ammonium thiosulfate, etc. or an ether solution of thiocyanogen, etc. is dropped to the sintered body. After drying, the sintered body was heated in atmosphere at 600° C. specifically, and at 400° C.~850° C. in general, for 10 minutes.

Next, a certain quantity of an aqueous solution of a compound of Ir or Ir—Pt, etc. was dropped to the sensor 2, and the sensor 2 was heated, for example, in atmosphere at 600° C. or at 500~850° C in general for 10 minutes and the compound was thermally decomposed to produce metallic Ir or Ir—Pt. Similarly, as controls, diluted sulfuric acid, aqueous solution of urea, etc. were dropped and gas sensors of controls were produced by heat treatment at 600° C. Ir was dropped as an aqueous solution of a nitrate. Pt was dropped as an aqueous solution of chloroplatinic acid, and Rh was dropped as an aqueous solution of a chloride. The form at the time of addition is arbitrary, and thermal decomposition temperature is, for example, from 500° C. to 850° C., and in place of thermal decomposition, reduction by hydrogen may be used to produce metal Ir, metal Ir—Pt, etc. The contents of S, Ir, etc. were derived from the quantities of the added liquids and their concentrations and converted into additions per 1 g of SnO2.

Figure 3:
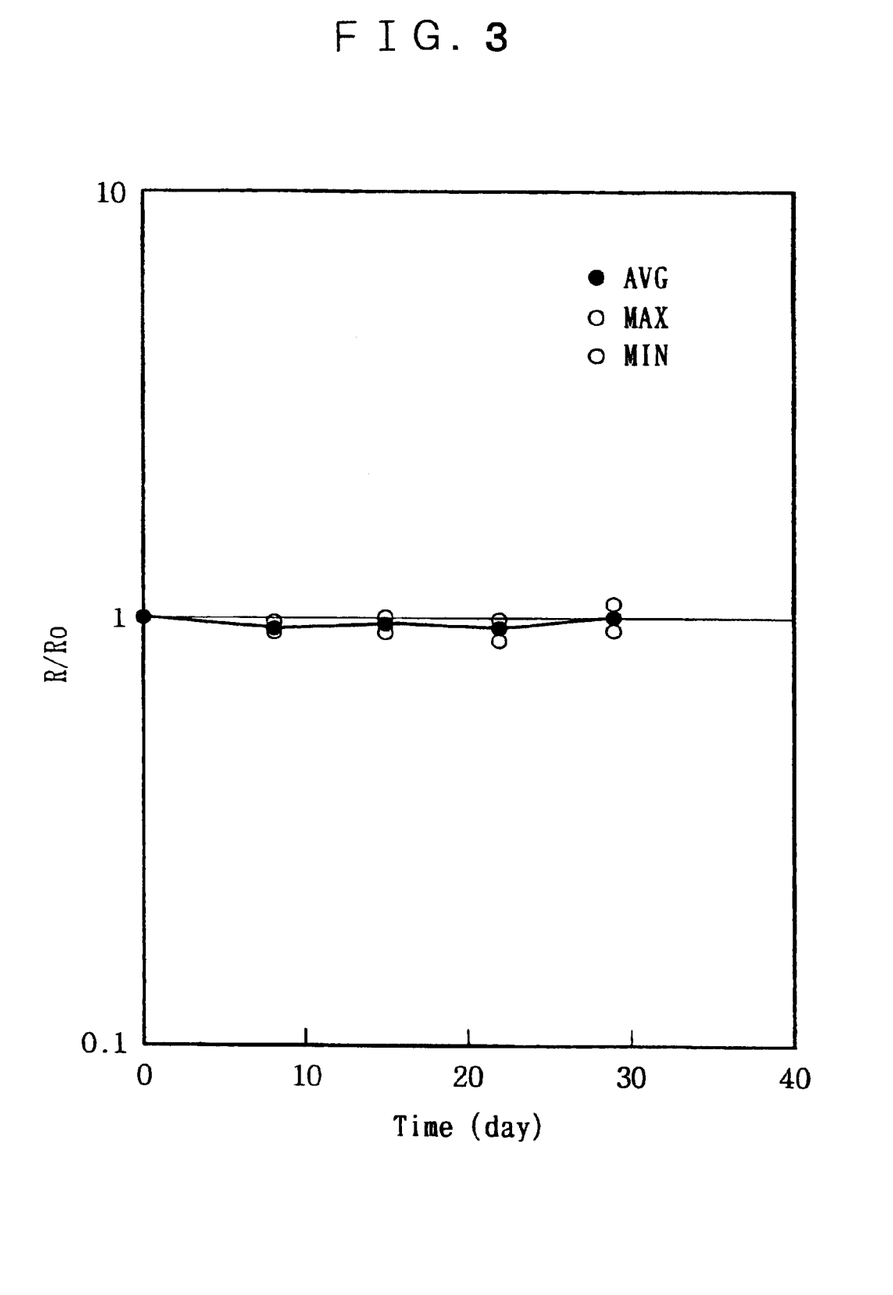
FIG. 3 is a characteristic diagram showing a long-term characteristic for one month of a gas sensor wherein 1 mg/gSnO2 of thiourea in reduction to simple S element is added.
Figure 4:
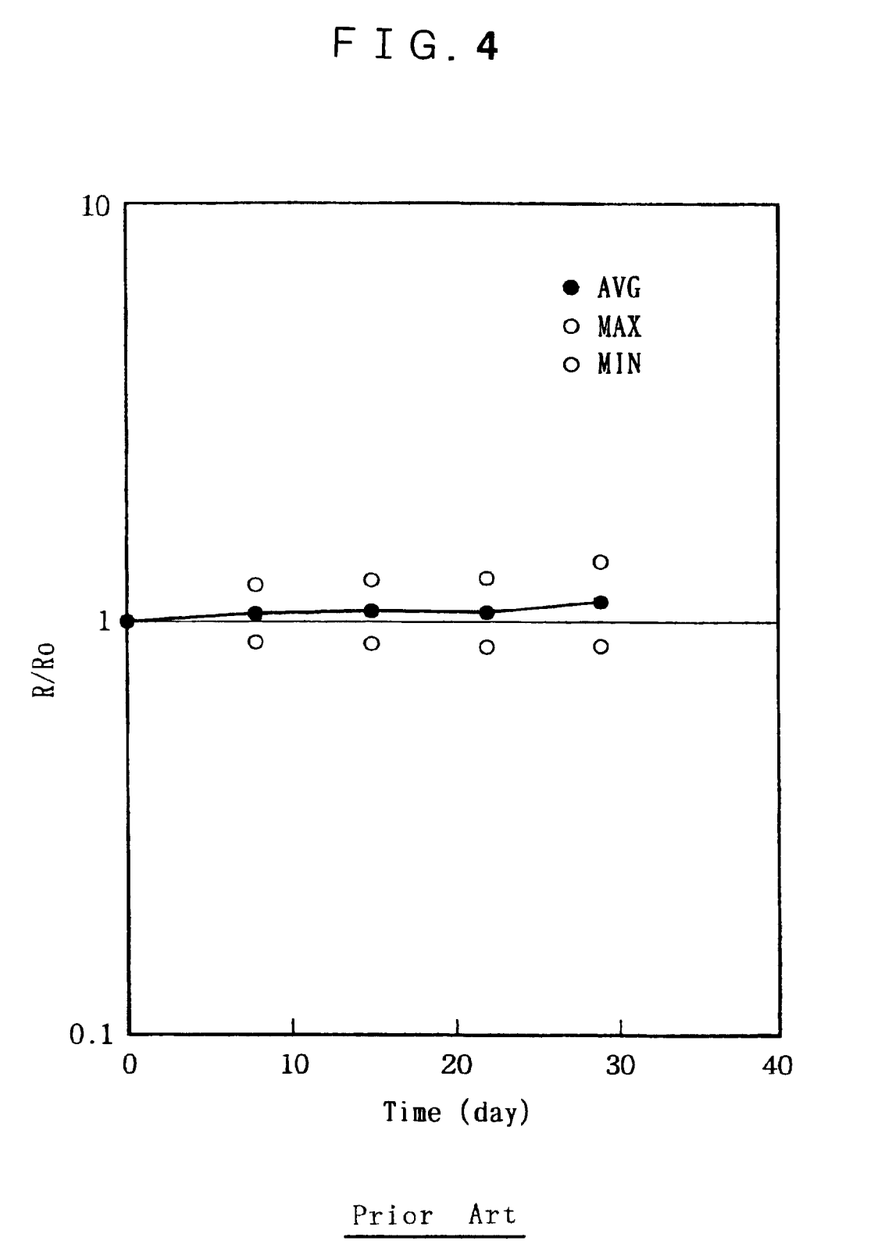
FIG. 4 is a characteristic diagram showing a long-term characteristic for one month of a prior art gas sensor wherein 0.4 mg/gSnO2 of sulfate ion in reduction to simple S element is added.
Figure 5:
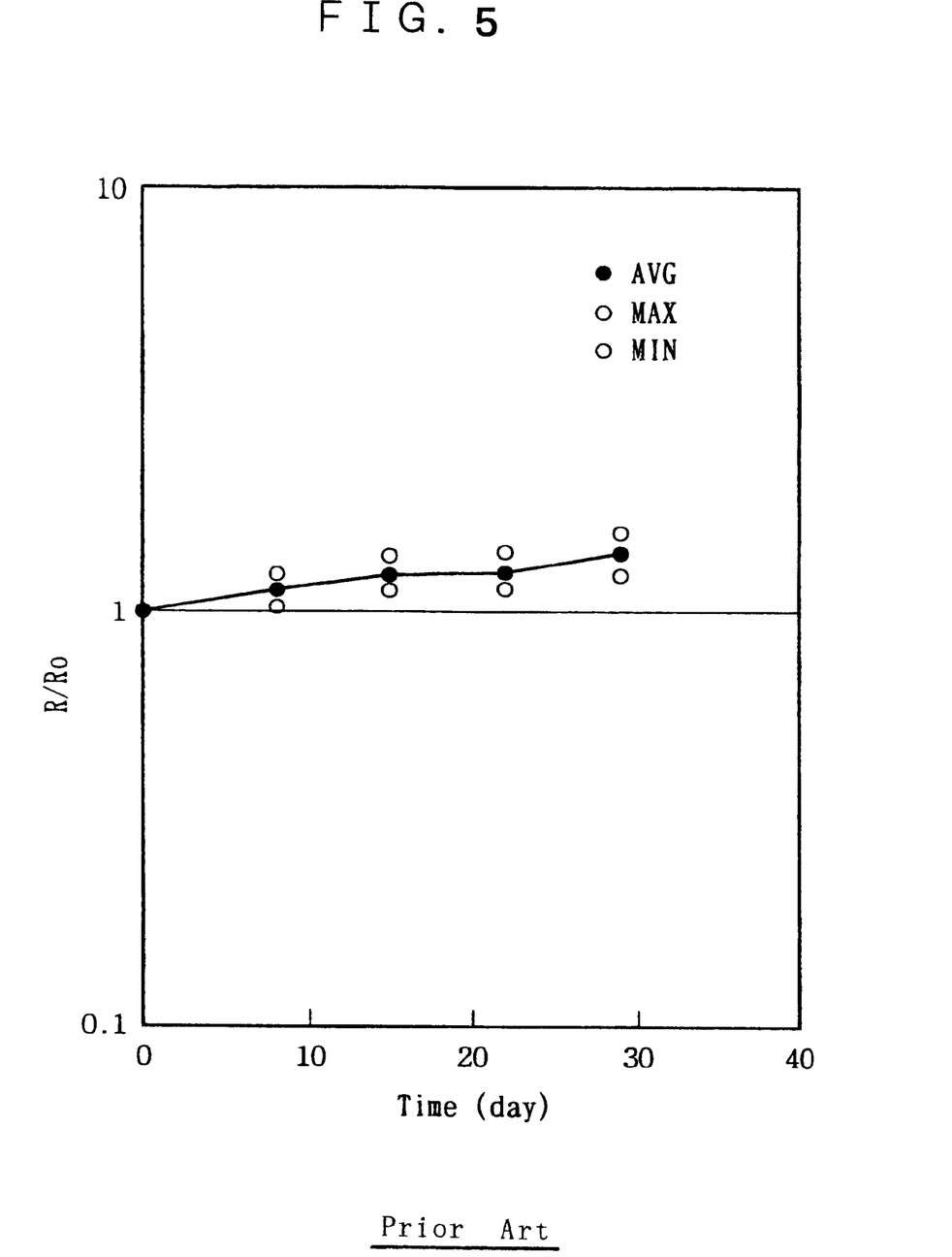
FIG. 5 is a characteristic diagram showing a long-term characteristic for one month of a prior art gas sensor wherein neither thiourea nor sulfate ion is added.

Each of the gas sensors 2 thus obtained was used under the above-mentioned service conditions for three days, then its resistance at 100 ppm of CO was measured for one month. The result was given as an average of measurements of five samples of each gas sensor 2. FIG. 3 shows the results of addition of 1 mg/gSnO2 of thiourea in reduction to simple S element. In the following, the quantity of addition of an S compound is indicated in reduction to simple S element, and mg/g SnO2 is simply expressed as mg/g. The number of samples in each measurement is 5 or 10, and the indicated value is an average. FIG. 4 shows the characteristic of a control wherein addition of sulfate ion was 0.4 mg/g. FIG. 5 shows the result of a prior art sensor wherein no S compound was added. The addition of thiourea can eliminate the long-term resistance increase completely, and its effect is much higher than that of sulfate ion.

Figure 6:
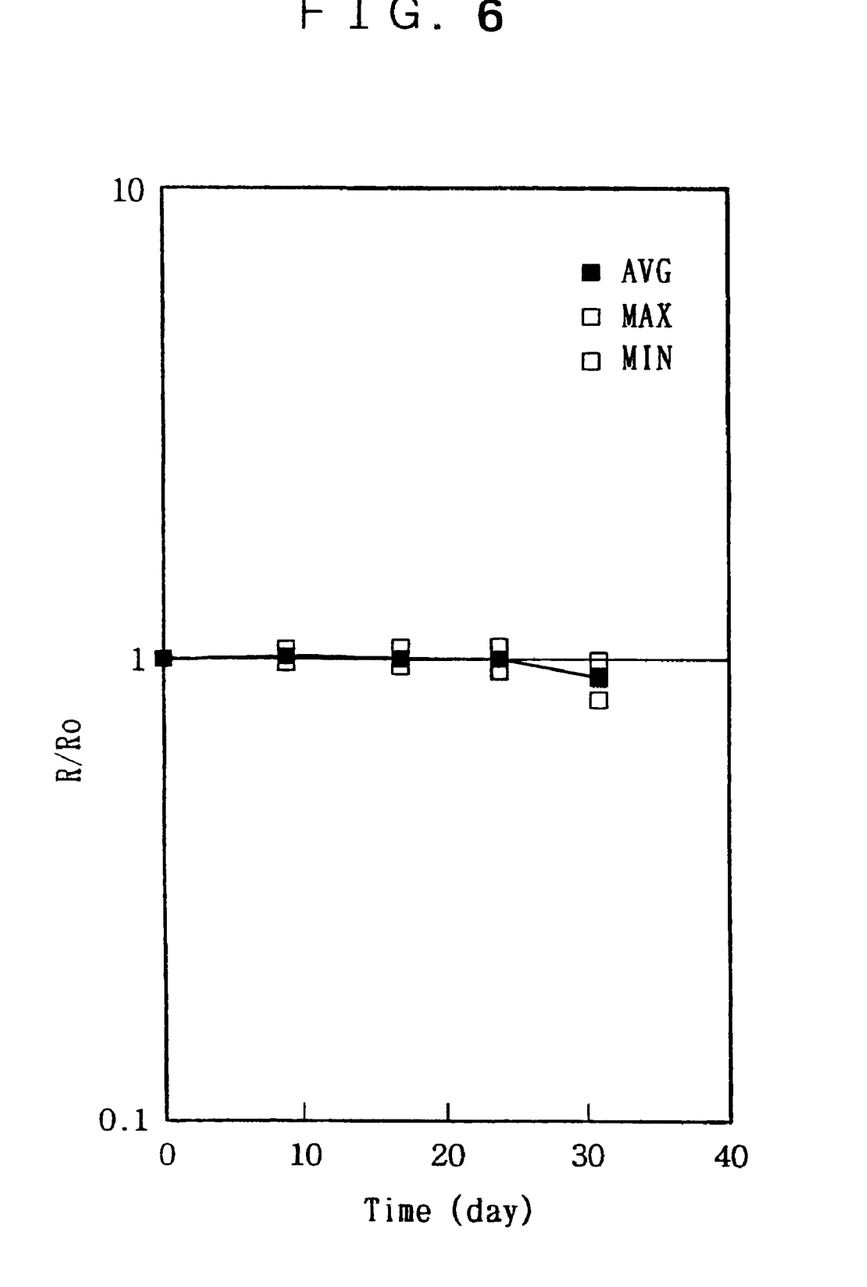
FIG. 6 is a characteristic diagram showing a long-term characteristic for one month of a gas sensor wherein both 1 mg/gSnO2 of thiourea in reduction to simple S element and 60 µg/gSnO2 of Ir are added.
Figure 7:
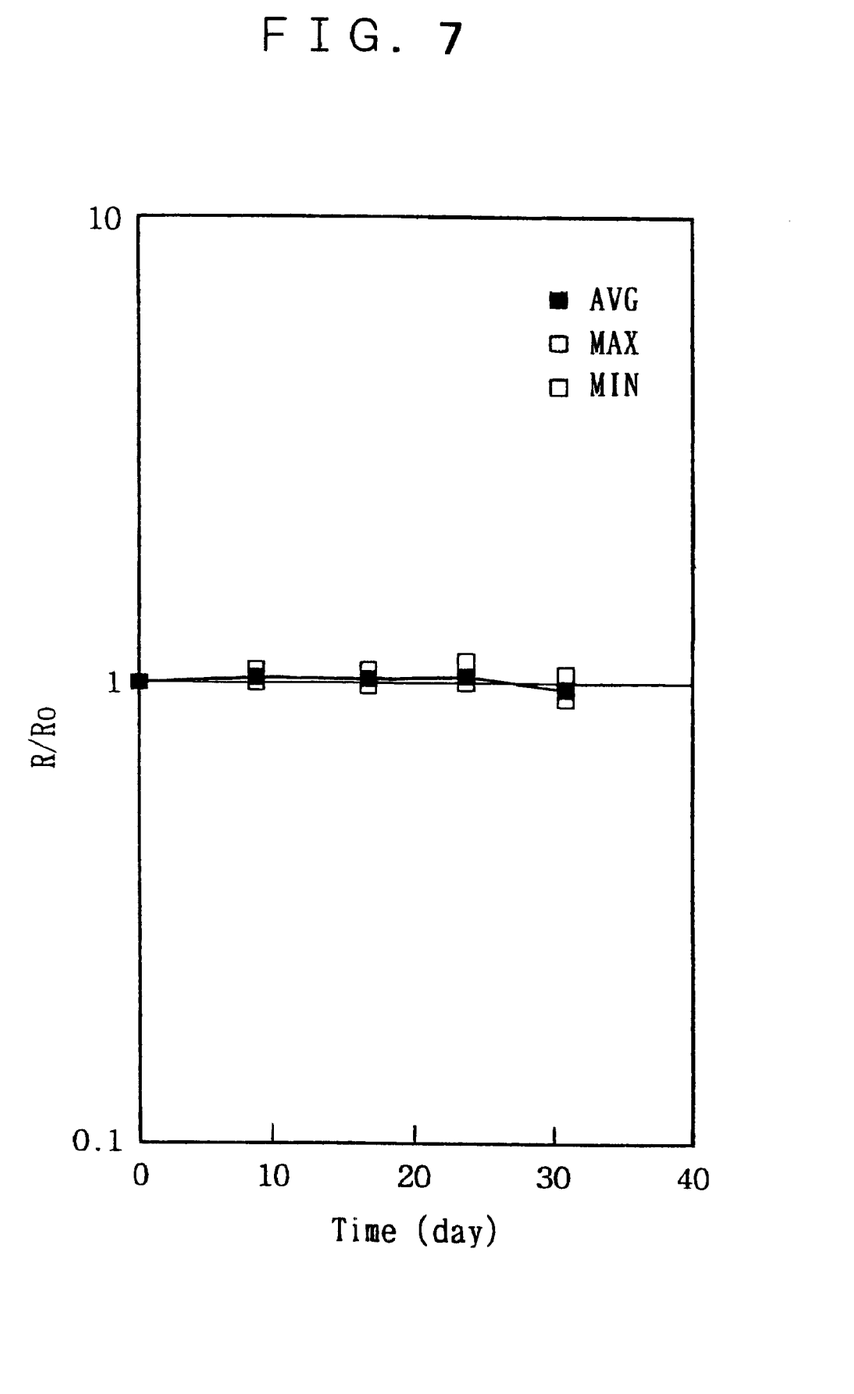
FIG. 7 is a characteristic diagram showing a long-term characteristic for one month of a gas sensor wherein 1 mg/gSnO2 of thiourea in reduction to simple S element, 60 µg/gSnO2 of Ir and 60 µg/gSnO2 of Pt in the form of an Ir—Pt compound catalyst are added.
Figure 8:
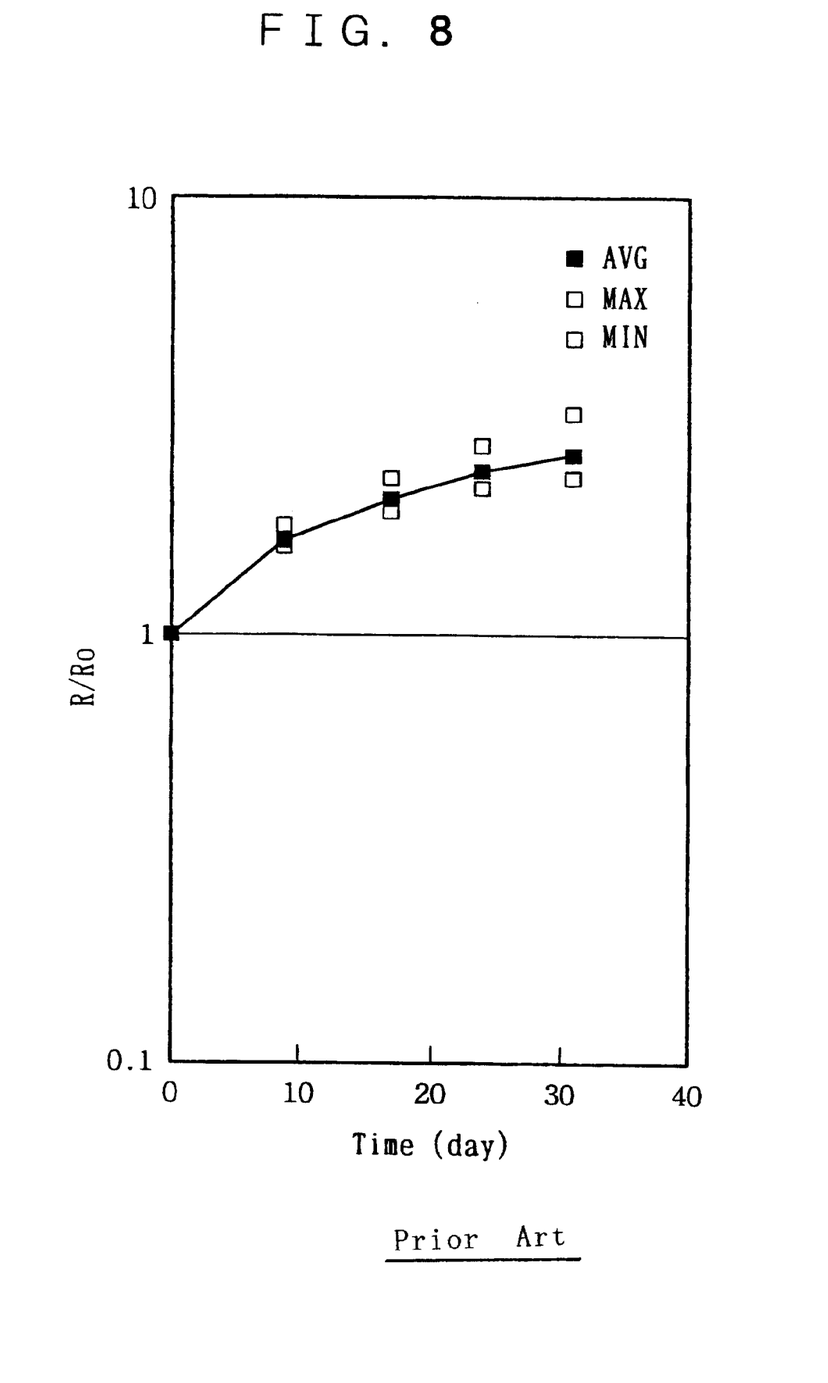
FIG. 8 is a characteristic diagram showing a long-term characteristic for one month of a prior art gas sensor wherein no thiourea is added and 60 µg/gSnO2 of Ir and 60 µg/gSnO2 of Pt in the form of an Ir—Pt compound catalyst are added.

Addition of Ir increases $\alpha$, and addition of Ir—Pt increases $\alpha$ and suppresses temperature and humidity dependency. They are accompanied by some side effects, namely, long-term resistance increase and initial increase in sensor resistance. Addition of an electron-donative S compound prevents this long-term resistance increase, and it also prevents increase in sensor resistance. FIG. 6 through FIG. 8 show the effects of S compounds in preventing long-term resistance increase. FIG. 6 shows a characteristic when Ir was added at 60 $\mu$g/g and an S compound (thiourea; this also applies if not specified otherwise in the following) was also added at 1 mg/g. FIG. 7 shows a characteristic when Ir and Pt were added at 60 μg/g each and an S compound was also added at 1 mg/g. FIG. 8 shows a characteristic when Ir and Pt were added at 60 μg/g each but no S compound was added. Addition of Ir—Pt generates long-term resistance increase. Addition of Ir alone also generates long-term resistance increase although this is not illustrated. In contrast to it, addition of an S compound prevents long-term resistance increase as shown in FIG. 6 and FIG. 7.

Figure 9:
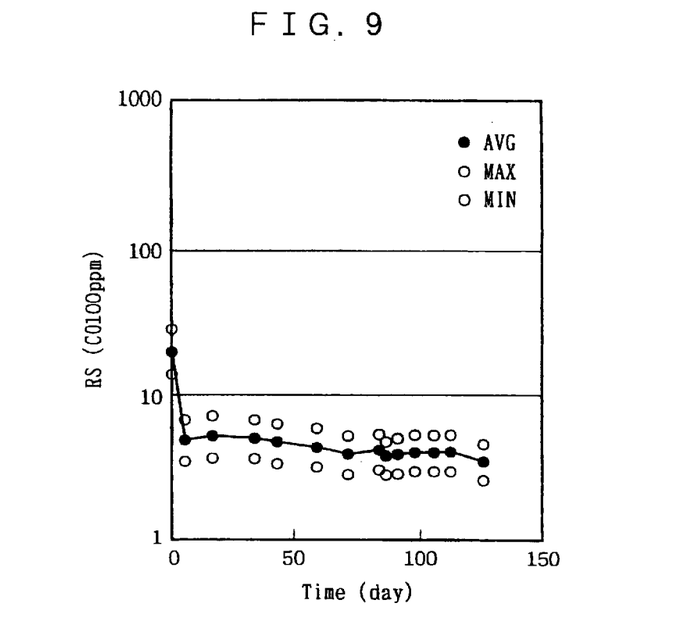
FIG. 9 is a characteristic diagram showing a long-term characteristic for four months of a gas sensor wherein 1 mg/gSnO2 of thiourea in reduction to simple S element is added.
Figure 10:
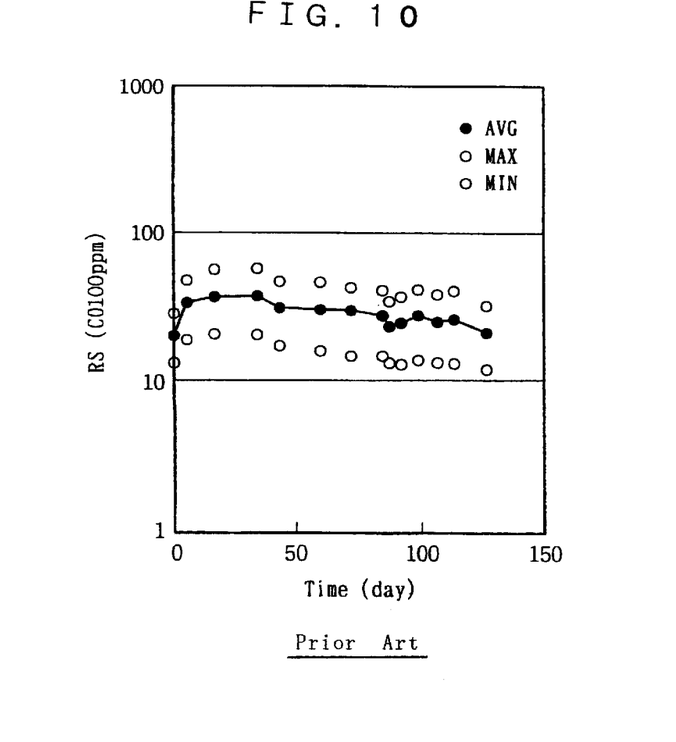
FIG. 10 is a characteristic diagram showing a long-term characteristic for four months of a prior art gas sensor wherein 5 mg/gSnO2 of urea is added.
Figure 11:
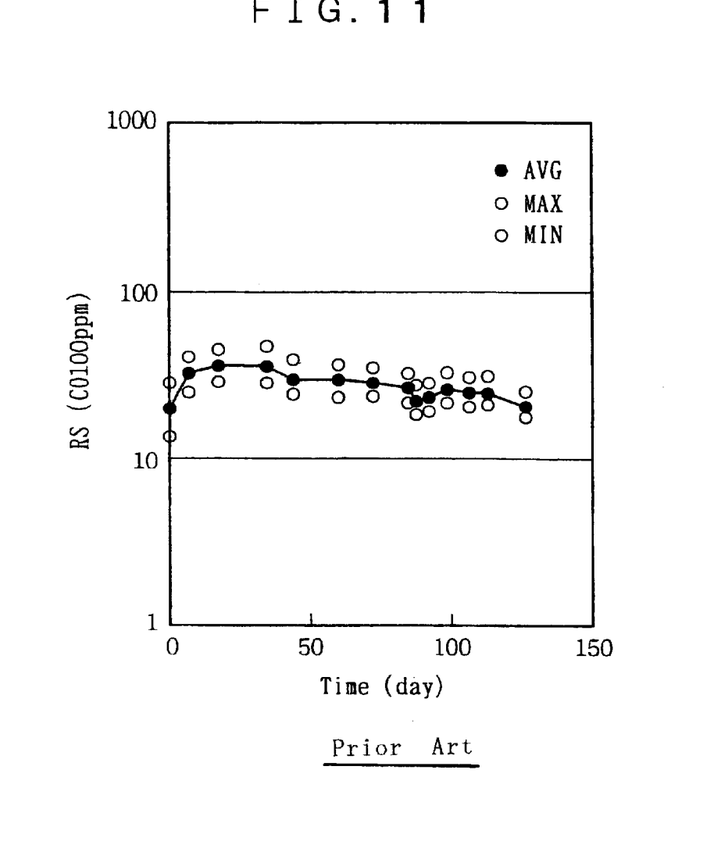
FIG. 11 is a characteristic diagram showing a long-term characteristic for four months of a prior art gas sensor wherein no thiourea nor urea is added.

FIG. 9 through FIG. 11 show behaviors of the sensor resistance at 100 ppm of CO for 4 months starting from a point shortly after the production. FIG. 9 shows the behavior of sensors wherein thiourea was added at 1 mg/g. FIG. 10 shows, for comparison, the behavior of sensors wherein urea was added at 5 mg/g in reduction to urea. FIG. 11 shows the behavior of prior art sensors wherein no urea nor thiourea is added. Thiourea generates a rapid resistance decrease immediately after the production, and the resistance is stable after that. As a result, the overall level of the resistance decreases by the drop in the resistance immediately after the production. This overall decrease in resistance compensates the resistance increase that is caused by addition of Ir, Ir—Pt, etc. The behavior when urea is added is comparable to the behavior when no urea nor thiourea is added (FIG. 1). Thus urea has no effect similar to that of thiourea.

Figure 12:
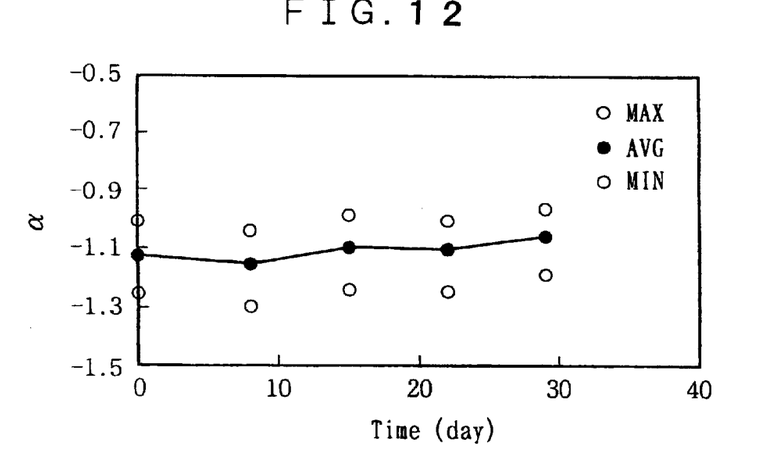
FIG. 12 is a characteristic diagram showing a long-term characteristic of CO concentration dependency α of a gas sensor wherein 1 mg/gSnO2 of thiourea in reduction to simple S element is added.
Figure 13:
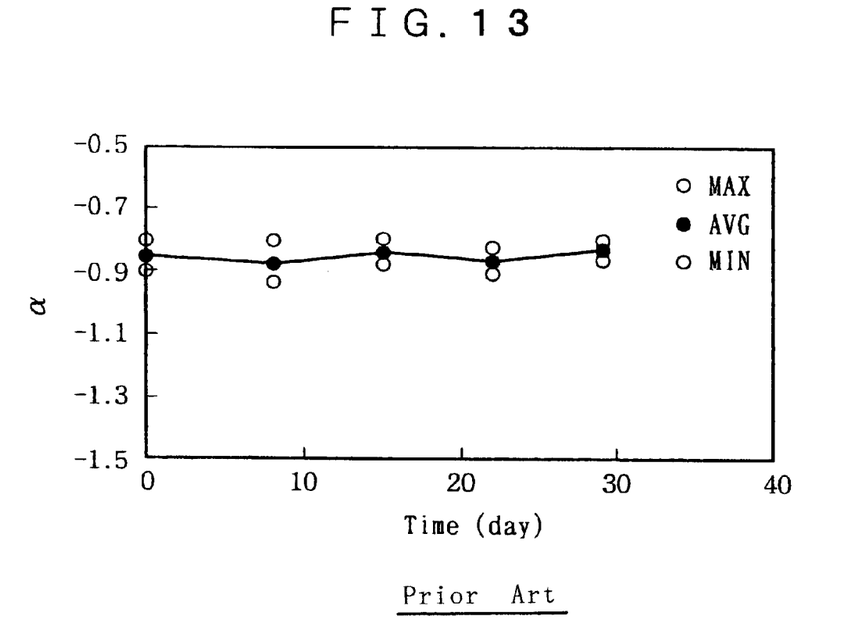
FIG. 13 is a characteristic diagram showing a long-term characteristic of CO concentration dependency α of a prior art gas sensor wherein 0.4 mg/gSnO2 of sulfate ion in reduction to simple S element is added.
Figure 14:
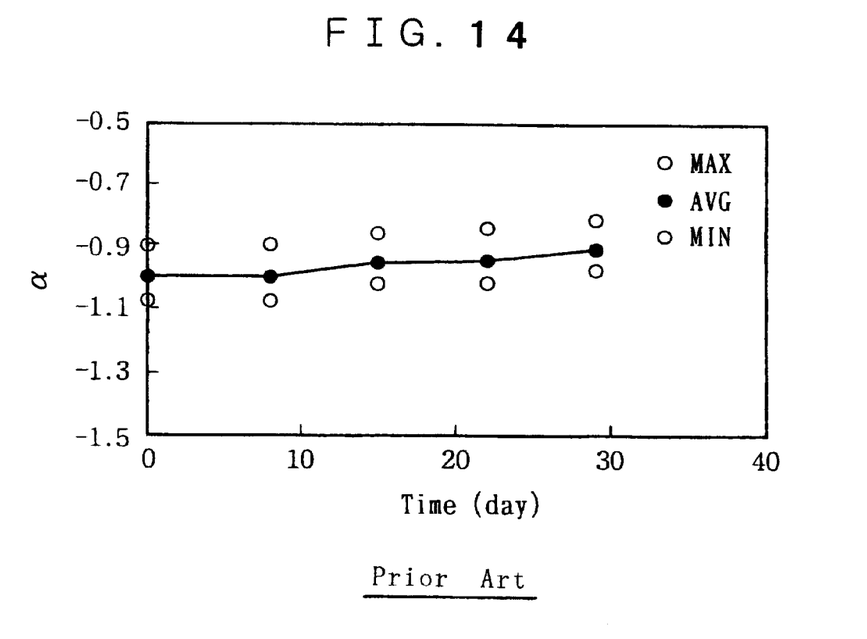
FIG. 14 is a characteristic diagram showing a long-term characteristic of CO concentration dependency α of a prior art gas sensor wherein no thiourea nor sulfate ion is added.

FIG. 12 through FIG. 14 show the behavior of α over the same period of FIG. 9 through FIG. 11. FIG. 12 shows the behavior when thiourea was added at 1 mg/g. FIG. 13 shows the behavior when sulfate ion was added at 0.4 mg/g. FIG. 14 shows behavior of a prior art sensor wherein no one of thiourea, urea and sulfate ion was added. Addition of sulfate ion decreases the absolute value of α and addition of thiourea increases the absolute value of α.

FIG. 15 through FIG. 18 show the temperature and humidity characteristics. The measured characteristics were the resistance at 100 ppm, 300 ppm and 1000 ppm of CO when the atmosphere was changed from 20° C. and relative humidity 65% to −10° C. (dew point: −12° C. approx.) and to 0° C. (due point: −5° C. approx.). The temperature and humidity dependency of the gas sensor is due to, for the most part, changes in the absolute humidity, and the temperature and humidity dependency is particularly large between around normal temperature and normal humidity and low temperature. Hence the temperature and humidity dependency for a range from 20° C. to −10° C. was measured.

Figure 15:
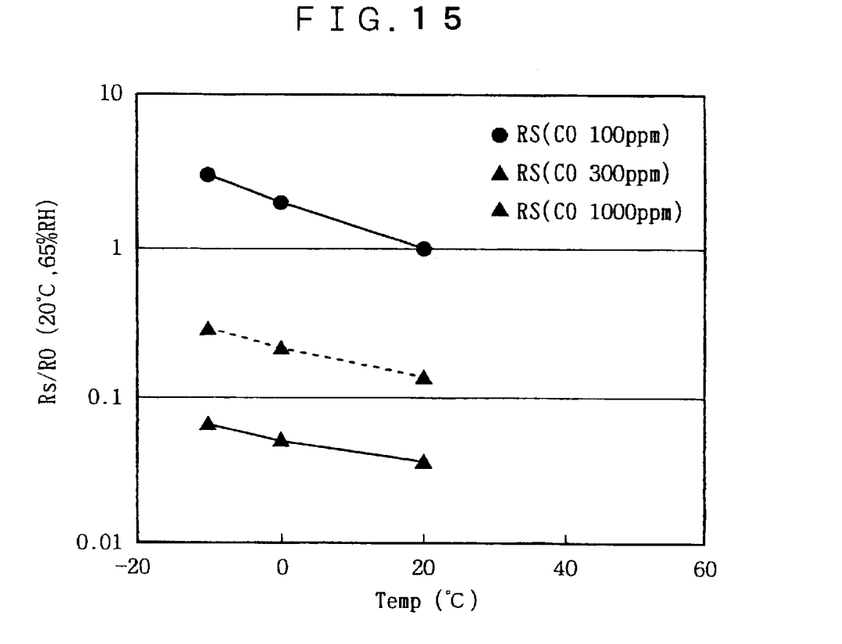
FIG. 15 is a characteristic diagram showing temperature and humidity dependency of a gas sensor wherein 1 mg/gSnO2 of thiourea and 60 µg/gSnO2 of Ir are added. The temperature range is from −10° C. to 20° C., and the CO concentration range is from 100 ppm to 1000 ppm.
Figure 16:
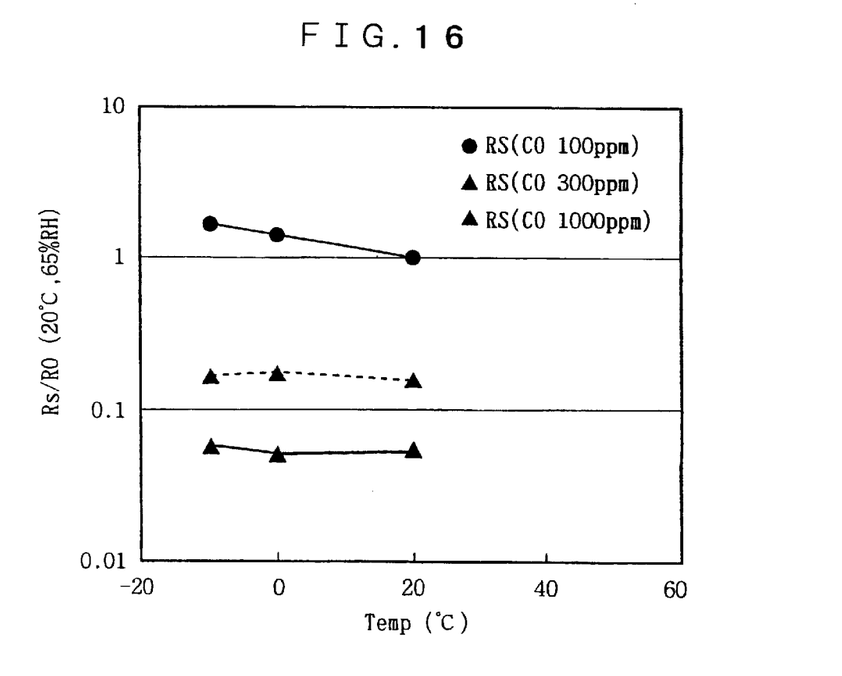
FIG. 16 is a characteristic diagram showing temperature and humidity dependency of a gas sensor wherein 0.5 mg/gSnO2 of thiourea and 60 µg/gSnO2 of Ir and 60 µg/gSnO2 of Pt in the form of an Ir—Pt compound catalyst are added. The temperature range is from −10° C. to 20° C., and the CO concentration range is from 100 ppm to 1000 ppm.
Figure 17:
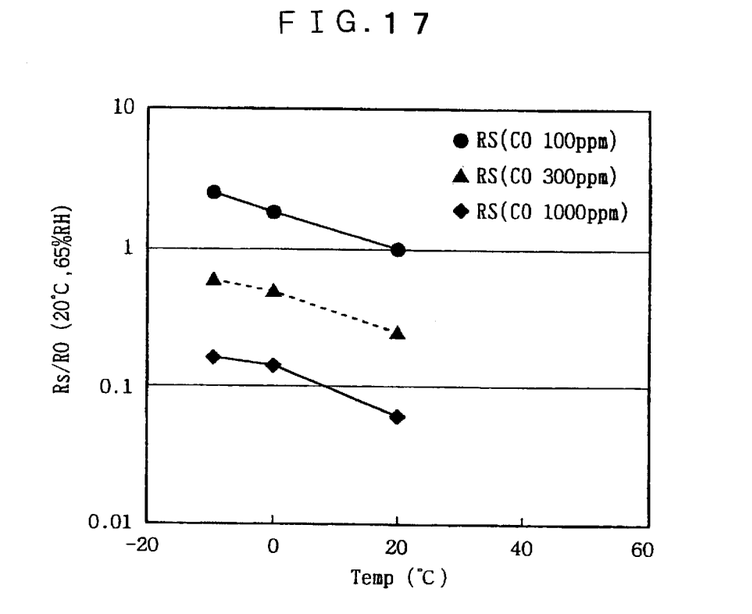
FIG. 17 is a characteristic diagram showing temperature and humidity dependency of a gas sensor wherein 1 mg/gSnO2 of thiourea is added. The temperature range is from −10° C. to 20° C., and the CO concentration range is from 100 ppm to 1000 ppm.
Figure 18:
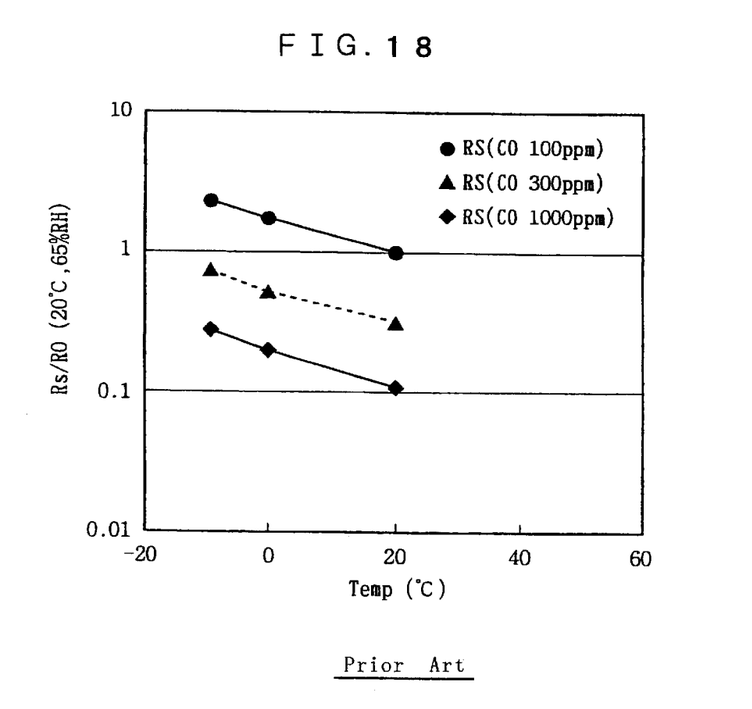
FIG. 18 is a characteristic diagram showing temperature and humidity dependency of a prior art gas sensor wherein no addition of thiourea, Ir or Pt is made. The temperature range is from −10° C to 20° C., and the CO concentration range is from 100 ppm to 1000 ppm.

FIG. 15 shows the characteristic when Ir was added at 60 μg/g and thiourea was added at 1 mg/g. Due to increase in a, errors due to changes in temperature and humidity decrease, but the resistance at 100 ppm of CO increased about three times when the atmosphere was changed from 20° C. to −10° C. This does not differ much from the characteristic of the prior art sensor of FIG. 18. FIG. 16 shows the characteristics when Ir and Pt were added at 60 μg/g each (Ir and Pt were added in the form of a mixed aqueous solution of Ir nitrate and chloroplatinic acid) and thiourea was added at 1 mg/g. α is large, and the temperature and humidity dependency is extremely small. FIG. 17 shows the results of the embodiment wherein thiourea was added at 1 mg/g and no Ir nor Pt was added. An increase in α is generated, but the temperature and humidity dependency itself is large. FIG. 18 shows the results of a prior art sensor wherein no one of thiourea, Ir and Pt was added. The output at 300 ppm CO at −10° C. is comparable to the output at about 140 ppm CO at 20° C.

The influences of thiourea, etc. are generally listed in Table 1. The table shows α that was determined for a range from 100 ppm to 1000 ppm of CO, the degree of the resistance increase at 100 ppm of CO for one month starting after three days of aging immediately after the production (the resistance after one month when the initial resistance is set at 1), and the value of resistance at 100 ppm of CO, 20° C. and relative humidity 65% (measured after use for three days immediately after production, and unit is kΩ).

TABLE 1

Influences of S Compounds

| Sample No. and addition of S compound (mg/g) | | α | Degree of the resistance increase (Rs/Rstd) | Sensor resistance (kΩ) |
| --- | --- | --- | --- | --- |
| 1 No addition | | 1.0 | 1.4 | 12 |
| 2 Thiourea | 0.02 | 1.0 | 1.2 | 10 |
| 3 Thiourea | 0.1 | 1.05 | 1.1 | 8 |
| 4 Thiourea | 0.4 | 1.1 | 1.0 | 7 |
| 5 Thiourea | 1 | 1.1 | 1.0 | 6 |
| 6 Thiourea | 2 | 1.1 | 1.0 | 5 |
| 7 Thiourea | 4 | 1.1 | 1.0 | 3 |
| 8 Thiourea | 8 | 1.1 | 1.0 | 2 |
| 9 Thiocyanogen | 1 | 1.1 | 1.0 | 7 |
| 10 Ammonium thiocyanate | 1 | 1.1 | 1.0 | 6 |
| 11 Ammonium thiosulfate | 2 | 1.1 | 1.0 | 5 |
| 12 Ethylmercaptan | 2 | 1.1 | 1.2 | 5 |
| 13 Thiophenol | 2 | 1.1 | 1.1 | 5 |
| 14 Sulfate ion | 0.4 | 0.9 | 1.2 | 8 |
| 15 Sulfate ion | 1 | 0.8 | 1.1 | 5 |

*Samples 14, 15 wherein S compound was added in the form of sulfate ion are controls.

Table 2 shows the use of thiourea as S compound, suppression of the temperature and humidity dependency by addition of Ir, Ir—Pt, etc., further increase in α, prevention of resistance increase by addition of Ir, etc. Thiourea was added at 1 mg/g SnO2, and the production conditions were as described above. The temperature and humidity dependency is indicated by a CO concentration which corresponds at 20° C., 65% to the sensor resistance which indicates 300 ppm of CO at −10° C. The table also shows α for a range from 100 to 1000 ppm of CO at 20° C., 65%, the rate of resistance increase after one month use in comparison to the initial value (Rs/Rstd), and the resistance (unit:kΩ) at 100 ppm of CO on the third day of use. Each result is the average of five sensors.

TABLE 2

Sensor Characteristics

| Sample No. and Catalyst quantity (μg/g) | Sensor resistance Rs (kΩ) | α | Temperature and humidity dependencey | Resistance increase (Rs/Rstd) |
| --- | --- | --- | --- | --- |
| 21 No addition of Ir, thiourea | 8 | 1.0 | 140 | 1.4 |
| 22 Ir 60 No thiourea | 22 | 1.5 | 200 | 2.2 |
| 23 No Ir, thiourea 1 mg/g | 4 | 1.1 | 150 | 1.0 |
| 24 Ir l0 | 6 | 1.3 | 180 | 1.2 |
| 25 Ir 60 | 8 | 1.5 | 200 | 1.0 |
| 26 Ir 120 | 12 | 1.5 | 210 | 0.95 |
| 27 Ir 400 | 60 | 1.5 | 210 | 0.9 |
| 28 Ir 60-Pt 60 | 18 | 1.4 | 280 | 0.95 |
| 29 Ir 60-Pt 15 | 10 | 1.4 | 250 | 1.0 |
| 30 Ir240-Pt 50 | 80 | 1.5 | 250 | 1.1 |

TABLE 2-continued

Sensor Characteristics

| Sample No. and Catalyst quantity (μg/g) | Sensor resistance Rs (kΩ) | α | Temperature and humidity dependencey | Resistance increase (Rs/Rstd) |
|---|---|---|---|---|
| 31 Ir100-Pt450 | 70 | 1.4 | 230 | 1.2 |
| 32 Pt 60 | 5 | 1.3 | 170 | 1.0 |

*If not specified otherwise, thiourea was added at 1 mg/g.

The present inventor added, in addition to the specimens mentioned above, Ir—Pd, Ir—Ru, Ir—Os, Ir—Re, Pt—Re, Pt—Pd, Ru, Os, etc. to the gas sensor 2 in a similar manner (addition was 60 μg/g per each element). However, no specimen exhibited suppresion of the temperature and humidity dependency. Although Table 2 show cases in which thiourea was added, addition of ammonium thiosulfate, ammonium thiocyanate or thiocyanogen (each addition at 1 mg/g in reduction to simple S element) produced results similar to those of Table 2. Addition of an electron-donative S compound is made after sintering of the metal oxide semiconductor. The reason is that the effects of the addition in the powder stage are small. In particular, addition in a stage when SnO2 is in the form of raw material (various tin compounds) is useless.

Addition of Phosphate Ion

Figure 19:
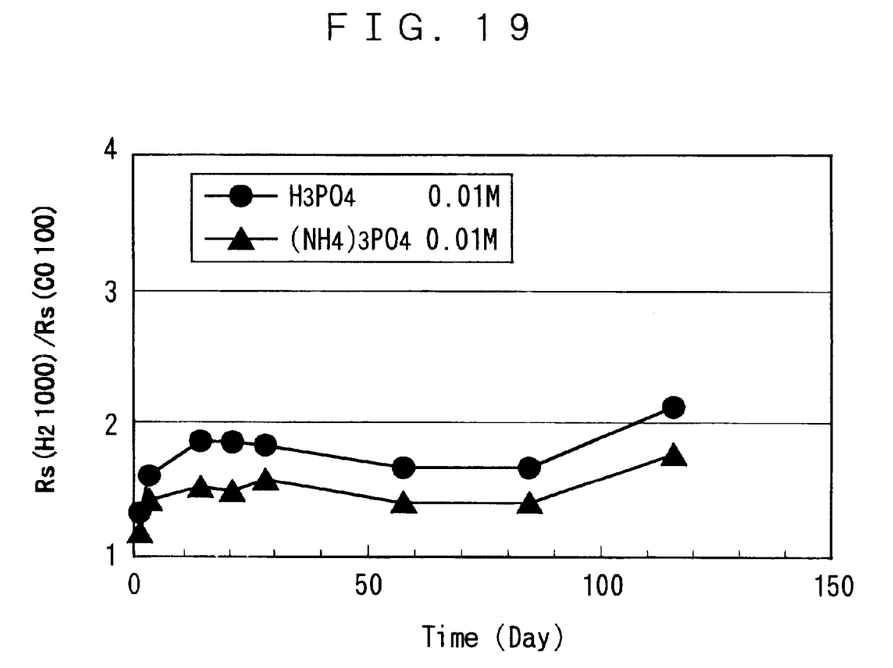
FIG. 19 is a characteristic diagram showing changes in relative sensitivity of a gas sensor to CO and hydrogen. In one gas sensor, 1 mg/gSnO2 of thiourea in reduction to simple S element is added, and further, 0.01 M (mol/l) of phosphoric acid is added. In the other gas sensor, 1 mg/gSnO2 of thiourea in reduction to simple S element is added, and further, 0.01 M (mol/l) of ammonium phosphate is added.

The gas sensor of FIG. 1 was used. The addition of thiourea was, in reduction to simple S element, at 1 mg/g SnO2, and a sensor wherein no Ir nor Ir—Pt was added was produced. The sensor was immersed in an aqueous solution of phosphoric acid (0.01 M) or an aqueous solution of antimony phosphate (0.01 M). After drying, the sensor was heat-treated at 600° C. for 10 minutes. In this way, phosphate ion was added to SnO2. It was confirmed that such a sensor exhibited an improved relative sensitivity to CO and hydrogen and that the addition had no adverse effects on the long-term characteristics of the sensor. The relative sensitivity to CO and hydrogen is defined by the ratio of the resistance at 1000 ppm of hydrogen to the resistance at 100 ppm of CO immediately before the end of the lower temperature period. Normally, this ratio is required to be not less than one, and the higher the ratio, the better sensitivity. The behaviors of the relative sensitivity to 100 ppm of CO and 1000 ppm of hydrogen over about 120 days after the production are shown in FIG. 19. The introduction of phosphate ion improves the relative sensitivity to CO and hydrogen.

As a result of experiments, it was found that addition of phosphate ion can be made by, after production of the sensor, immersing the sensor in a solution containing 0.001 M~0.2 M of phosphate ion, particularly in an aqueous solution, and after that, heat-treating the sensor at 500~800° C.

What is claimed is:

1. A CO sensor for detecting CO including a metal oxide semiconductor comprising a $SnO_2$ gas sensitive material and a means to subject said metal oxide semiconductor to cyclical temperature change, wherein an electron-donative S compound having a double-bonded sulfur atom with an oxidation number of −2 is added to said $SnO_2$ at 0.01–10 mg/g $SnO_2$ in reduction to simple S element.

2. A CO sensor of claim 1 characterized in that the addition of said S compound is 0.1~5 mg/g SnO2 in reduction to simple S element.

3. A CO sensor of claim 1 characterized in that said electron-donative sulfur compound is at least one member of a group consisting of thiourea and its derivatives, thiosulfuric acid and its derivatives, thiocyanic acid and its derivatives, thiocyanogen and its derivatives, thiol, thiophenol, thioether, thiosugar and its derivatives, thiophene and its derivatives, thionaphthene and its derivatives, thiotolene and its derivatives, thiopyran and its derivatives, thiophthene and its derivatives, thioacetazone and its derivatives, thioxene and its derivatives, thioacetal and its derivatives, thioindigo and its derivatives, thiooxine and its derivatives, thiocarbazide and its derivatives, thiokinase, thioiglucosidase and CS2.

4. A CO sensor of claim 1 characterized in that Ir is added to said SnO2 at 5~500 μg/g SnO2 in reduction to metal.

5. A CO sensor of claim 4 characterized in that said Ir is added in the form of an Ir—Pt compound catalyst wherein the additions of Ir and Pt are respectively 5~500 μg/gSnO2 in reduction to metal, and the weight ratio of Ir to Pt is from 1/5 to 5.

6. A CO sensor of claim 1 characterized in that phosphate ion is added to said SnO2.

7. A method of producing a CO sensor comprising sintering $SnO_2$ powder to form a gas sensitive metal oxide semiconductor material, and then adding an electron-donative S compound having a double-bonded sulfur atom with an oxidation number of −2 at 0.01–10 mg/g SnO2 in reduction to simple S element.

8. A method of producing a CO sensor of claim 7 characterized in that a solution of said electron-donative sulfur compound is impregnated into a sintered body of SnO2, and after that, the sintered body is dried and heat-treated.

9. A method of producing a CO sensor of claim 8 characterized in that both Ir and Pt, 5~500μg/gSnO2 in reduction to metal each, are added, and the weight ratio of Ir/Pt being from 1/5 to 5, by impregnating a mixed solution of an Ir compound and a Pt compound into said sintered body of SnO2, then decomposing the Ir compound and the Pt compound impregnated.

10. A CO sensor for detecting CO including a metal oxide semiconductor comprising a $SnO_2$ gas sensitive material and means to subject said metal oxide semiconductor to cyclical temperature change,
wherein an electron-donative S compound of at least one member of a group consisting of thiourea, thiosulfuric acid and its derivatives, thiocyanic acid and its derivatives, thiocyanogen and its derivatives is added to said $SnO_2$ at 0.01–10 mg/g $SnO_2$ in reduction to simple S element.

* * * * *